US009198993B2

(12) United States Patent
Lin

(10) Patent No.: US 9,198,993 B2
(45) Date of Patent: Dec. 1, 2015

(54) ELECTRONIC INCENSE AND ELECTRONIC INCENSE CENSER HAVING THE SAME

(71) Applicant: HON HAI PRECISION INDUSTRY CO., LTD., New Taipei (TW)

(72) Inventor: Chen-Han Lin, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 20 days.

(21) Appl. No.: 14/014,394

(22) Filed: Aug. 30, 2013

(65) Prior Publication Data

US 2014/0177205 A1 Jun. 26, 2014

(30) Foreign Application Priority Data

Dec. 26, 2012 (TW) .............................. 101150292 A

(51) Int. Cl.
| | | |
|---|---|---|
| *F21V 33/00* | (2006.01) | |
| *A61L 9/00* | (2006.01) | |
| *A61L 2/00* | (2006.01) | |
| *F21W 121/00* | (2006.01) | |
| *F21Y 101/02* | (2006.01) | |
| *F21V 8/00* | (2006.01) | |

(52) U.S. Cl.
CPC ... *A61L 9/00* (2013.01); *A61L 2/00* (2013.01); *F21V 33/0028* (2013.01); *F21W 2121/00* (2013.01); *F21Y 2101/025* (2013.01); *G02B 6/0096* (2013.01)

(58) Field of Classification Search
CPC .............. F21V 33/0028; G02B 6/0096; G02B 6/02304; G02B 6/02328
USPC ..................... 362/96, 551, 553; 422/120, 125
See application file for complete search history.

(56) References Cited

U.S. PATENT DOCUMENTS

| 3,644,725 | A * | 2/1972 | Lochridge, Jr. ............... 362/556 |
|---|---|---|---|
| 3,681,588 | A * | 8/1972 | Lee ............................... 362/569 |
| 5,497,440 | A * | 3/1996 | Croitoru et al. ............... 385/125 |
| 7,278,769 | B2 * | 10/2007 | Dick .............................. 362/553 |
| 8,137,630 | B2 * | 3/2012 | Jorgensen ..................... 422/123 |
| 2006/0227574 | A1 * | 10/2006 | Chien ........................... 362/641 |
| 2007/0242924 | A1 * | 10/2007 | Cianciotto et al. ............ 385/133 |
| 2009/0257242 | A1 * | 10/2009 | Wendman ...................... 362/553 |
| 2010/0053970 | A1 * | 3/2010 | Sato et al. ...................... 362/259 |
| 2010/0124243 | A1 * | 5/2010 | Hussell et al. ............. 372/45.01 |

(Continued)

OTHER PUBLICATIONS

Michael A. Golub, Laser Beam Splitting bt Diffractive Optics, Feb. 2004, Optics & Photonics News pp. 37-41.*

(Continued)

*Primary Examiner* — Karabi Guharay
(74) *Attorney, Agent, or Firm* — Novak Druce Connolly Bove + Quigg LLP

(57) ABSTRACT

An electronic incense includes a hollow tube, a laser light source arranged at a light incident end of the hollow tube, and a light outputting portion arranged at a light output end of the hollow tube. The light emitting portion contacts and covers the light output end of the hollow tube for diverging light from the laser light source. The light generated by the laser light source moves directly through a void in the hollow tube to reach the light outputting portion without a guidance of a light guiding medium, for example, an optical fiber in the hollow tube. An electronic incense including a plurality of electronic incenses which share light from a single laser light source is also provided.

13 Claims, 2 Drawing Sheets

(56) References Cited

U.S. PATENT DOCUMENTS

2011/0310587 A1* 12/2011 Edmond et al. .................. 362/84
2014/0167625 A1* 6/2014 Tseng ........................... 315/158

OTHER PUBLICATIONS

Laser Beam Splitting by Diffractive Optics, Michael A. Golub, Feb. 2004 ∎ Optics & Photonics News.*

* cited by examiner

ELECTRONIC INCENSE AND ELECTRONIC INCENSE CENSER HAVING THE SAME

BACKGROUND

1. Technical Field

The present disclosure generally relates to an electronic incense, and particularly to an electronic incense having a laser light source providing light for the electronic incense and an electronic incense censer having a plurality of electronic incenses sharing a common laser light source.

2. Description of the Related Art

Incenses are lightened for religion affairs. A traditional incense mainly includes a rod made of bamboo and aromatic biotic materials coated on the rod. When the aromatic biotic materials are burned, they release a large amount of smoke. The burning incenses could ignite other articles to burn which may cause fire; furthermore, the released smoke not only pollutes the environment, but also is harmful to human health.

Accordingly, an electronic incense is used to replace the traditional incense. The electronic incense includes a rod which is made of optical fiber and a sheath coated on an outer surface of the rod. The sheath has an appearance in color like that of the aromatic biotic materials of the traditional incense. Light (usually red in color) from a light emitting diode (LED) light source is collected by a bottom end of the rod, and the rod transfers the light to illuminate a top end of the rod, thereby simulating the burning of the traditional incense. However, the cost of manufacturing the electronic incense with a rod made of optical fiber is high since the optical fiber is expensive. Furthermore, the conventional electronic incense censer which needs a number of LED light sources to provide light to a corresponding number of electronic incenses in the censer is high and has a complicated structure.

Therefore, it is desirable to provide an electronic incense and an electronic incense censer which can overcome the above-described problems.

BRIEF DESCRIPTION OF THE DRAWINGS

Many aspects of the disclosure can be better understood with reference to the drawings. The components in the drawings are not necessarily drawn to scale, the emphasis instead being placed upon clearly illustrating the principles of the present electronic incense and electronic incense censer. Moreover, in the drawings, all the views are schematic, and like reference numerals designate corresponding parts throughout the views.

DETAILED DESCRIPTION

Figure 1:
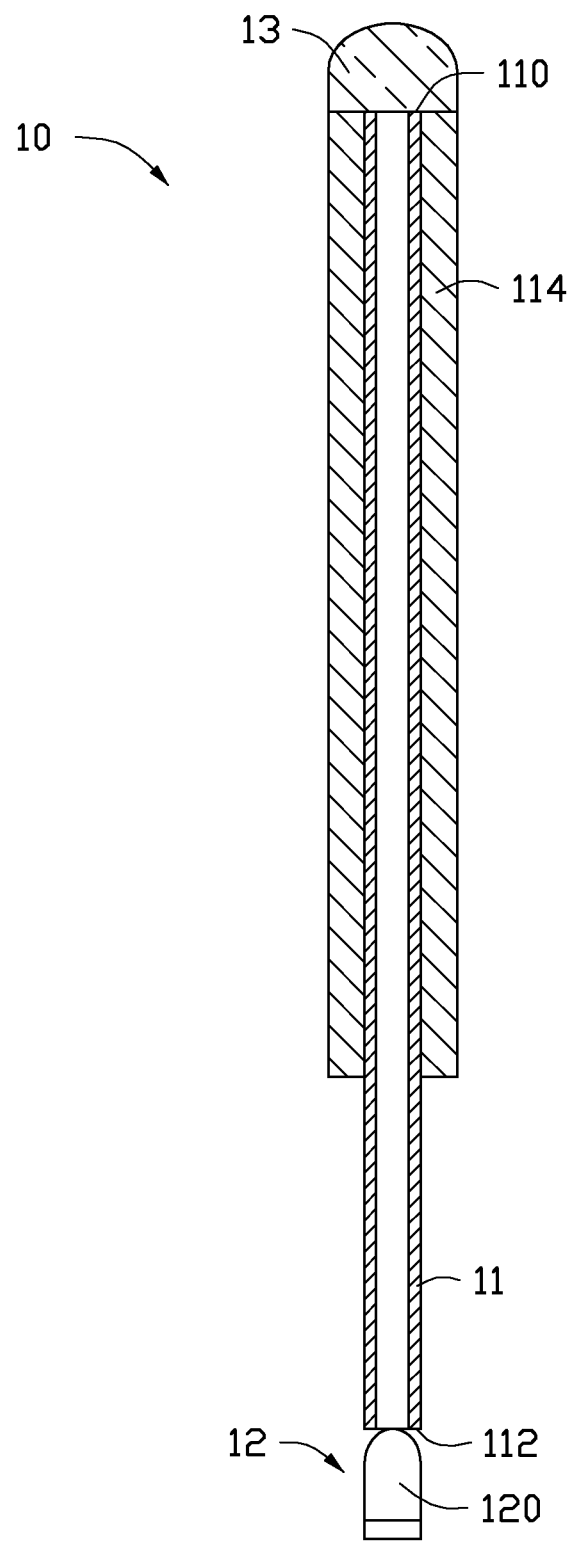
FIG. 1 is a cross-sectional view of an electronic incense in accordance with an exemplary embodiment of the present disclosure.

Referring to the FIG. 1, an electronic incense 10 in accordance with an exemplary embodiment of the present disclosure is provided. The electronic incense 10 includes a hollow tube 11, a laser light source 12 and a light outputting portion 13.

The hollow tube 11 is elongated and cylindrical. The hollow tube 11 includes a top end 110 for radiating light and a bottom end 112 for guiding light from the laser light source 12 thereinto. The hollow tube 11 is opaque, and the light of the laser light source 12 transmits from the bottom end 112 to the top end 110 of the hollow tube 11. In this embodiment, a sheath 114 is coated at an outer sidewall of the hollow tube 11 for further preventing light of the laser light source 12 from leaking out of the hollow tube 11. Preferably, a color of the sheath 114 is similar to that of the aromatic biotic materials of the traditional incense to simulate an external appearance of the traditional incense. The hollow tube 11 and the sheath 114 can made of any suitable materials only if the light of the laser light source could transmit from the bottom end 112 to the top end 110 of the hollow tube 11.

The laser light source 12 is arranged below the bottom end 112 of the hollow tube 11 for providing a laser beam into the hollow tube 11. In this embodiment, the laser light source 12 is a laser LED 120. In this embodiment, the laser LED 120 is arranged at the bottom end 112 and partly embedded in the hollow tube 11. Due to a high linearity of laser beam of the laser light source 12, the laser beam from the laser LED 120 can directly emit from the bottom end 112 through the hole in the hollow tube 11 to the top end 110 of the hollow tube 11 without a guidance of a light guiding media, for example, an optical fiber in the hollow tube 11. Accordingly, the electronic incense 10 in accordance with the present disclosure can have a lower cost.

The light outputting portion 13 is arranged at the top end 110 of the hollow tube 11 and covers the top end 110 of the hollow tube 11. The light outputting portion 13 is made of transparent materials, such as glass, resin and so on. A surface of the light outputting portion 13 is roughened so that light radiating out from the surface of the top end 110 can be diverged to different orientations for simulating the burning top end of the traditional incense when it is burned.

The top end 110 of the hollow tube 11 can be partly or totally covered by the light outputting portion 13 so that the laser beam can be transferred to the light outputting portion 13. In this embodiment, the top end 110 of the hollow tube 11 is totally covered by the light outputting portion 13.

Since the electronic incense 10 includes a laser light source 12, and the laser light source 12 generates laser beam with a high convergency (linearity), as such there is no need to provide an expensive optical fiber for guiding and concentrating divergent light from the traditional light source, whereby the manufacturing cost of the electronic incense 10 can be lowered down.

Figure 2:
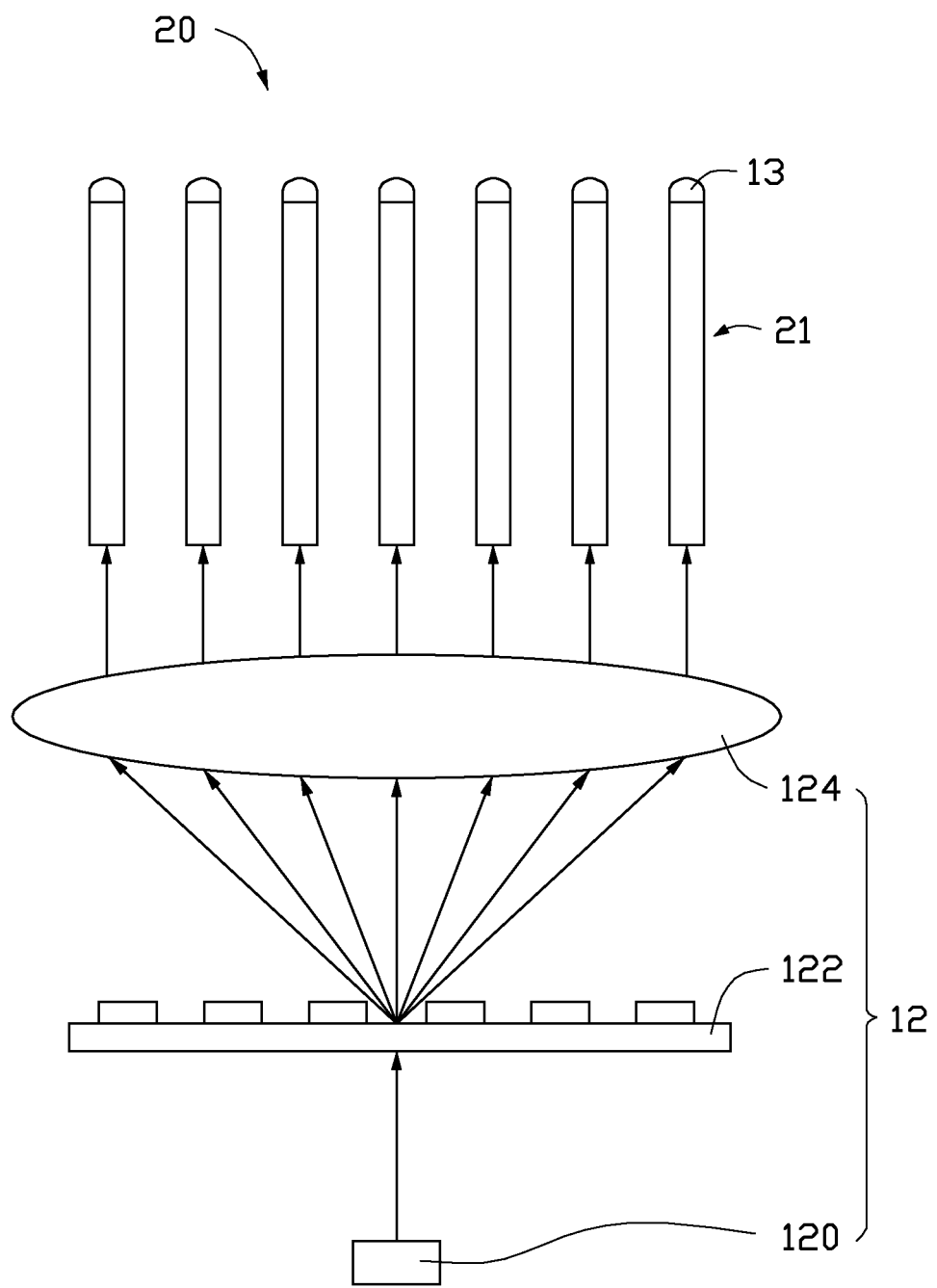
FIG. 2 is an isometric, diagrammatic view of an electronic incense censer in accordance with an exemplary embodiment of the present disclosure.

Referring to FIG. 2, an electronic incense censer 20 in accordance with an exemplary embodiment is provided.

The electronic incense censer 20 includes a plurality of electronic incenses 21 each are similar to the electronic incense 10 of FIG. 1. The difference is that the electronic incenses 21 share a common laser light source 12 including a laser LED 120. The laser light source 12 of the electronic incense censer 20 further includes a diffraction grating 122 and a concentrating lens 124. Each of the electronic incenses 21 includes a hollow tube (not labeled) and a light outputting portion 13. The plurality of electronic incense 21 are parallel to each other.

The diffraction grating 122 is arranged on a light outputting path of the laser LED 120 for dividing the single laser beam generated by the laser LED 120 to multiple laser beams. In this embodiment, the laser LED 120 faces to a center of the diffraction grating 122. The number of the electronic incenses 21 designated to be accommodated by the electronic incense censer 20 can be decided according a diffraction order "m" of the diffraction grating 122. The diffraction order "m" satisfies an equation: $m\lambda = \Lambda(n_2 \sin\theta_{dif} - n_1 \sin\theta_{inc})$, wherein "$\lambda$" represents a wavelength of the laser beam, "$\Lambda$" represents a diffraction period of the diffraction grating 122, "$n_1$" represents a refractive index of a medium for transferring an incident laser, "$n_2$" represents a refractive index of a medium for transferring a diffraction laser, "$\theta_{inc}$" represents an incident angle of the incident laser, and "$\theta_{dif}$" represents a diffraction angle of the diffraction laser.

The concentrating lens 124 is arranged on a light outputting path of the diffraction grating 122 for concentrating the multiple laser beams split by the diffraction grating 122. Thereafter the concentrated multiple laser beams respectively enter the plurality of hollow tubes of the electronic incenses 21. In this embodiment, a center of the concentrating lens 124 is aligned with the center of the diffraction grating 122, as such the multiple laser beams from the concentrating lens 124 are parallel to each other and respectively enter the corresponding hollow tubes of the electronic incenses 21.

It is to be understood that the above-described embodiments are intended to illustrate rather than limit the disclosure. Variations may be made to the embodiments without departing from the spirit of the disclosure. The above-described embodiments illustrate the scope of the disclosure but do not restrict the scope of the disclosure.

What is claimed is:

1. An electronic incense comprising:
   a hollow tube having a light incident end and an opposite light output end;
   a laser light source arranged at the light incident end of the hollow tube;
   a sheath coated on an outer sidewall of the hollow tube a color of the sheath is the color of the aromatic biotic materials of a traditional incense to simulate an external appearance of the traditional incense; and
   a light outputting portion arranged at the light output end of the hollow tube, the light outputting portion contacting and covering the light output end for diverging light from the laser light source, the light from the laser light source moving directly through a void in the hollow tube from the light incident end to the opposite light output end, the sheath preventing light of the laser light source from leaking out of the hollow tube.

2. The electronic incense of claim 1, wherein a surface of the light outputting portion is roughened.

3. The electronic incense of claim 1, wherein the laser light source is a laser light emitting diode (LED).

4. The electronic incense of claim 3, wherein the laser LED has an end portion embedded in the light incident end of the hollow tube.

5. The electronic incense of claim 1, wherein the top end of the hollow tube and the sheath coated on an outer sidewall of the hollow tube is totally covered by the light outputting portion.

6. An electronic incense censer comprising:
   a plurality of hollow tubes each having a light incident end and an opposite light output end;
   a laser light source located near the light incident ends of the hollow tubes;
   a sheath coated on an outer sidewall of each hollow tube a color of the sheath is the color of the aromatic biotic materials of a traditional incense to simulate an external appearance of the traditional incense; and
   a light outputting portion arranged at the light output end of each of the hollow tubes, the light outputting portion contacting and covering the light output end for diverging light from the laser light source, the light from the laser light source moving directly through a void in each of the hollow tubes from the light incident end to the opposite light output end thereof, the sheaths preventing light of the laser light source from leaking out of the hollow tubes.

7. The electronic incense censer of claim 6, wherein the laser light source comprises a laser LED, a light splitter and a light calibrator, the light splitter being arranged at a light outputting path of the laser LED to split a single laser beam from the laser LED into multiple laser beams, the light calibrator calibrating the multiple laser beams to respectively enter the hollow tubes.

8. The electronic incense censer of claim 7, wherein the light splitter is a diffraction grating.

9. The electronic incense censer of claim 8, wherein a diffraction order "m" of the diffraction grating satisfies a equation: $m\lambda 2=\Lambda(n2\sin\theta dif-n1\sin\theta inc)$, "$\lambda$" representing a wavelength of the laser beam, "$\Lambda$" representing a diffraction period of the diffraction grating, "$n_1$" representing a refractive index of a medium for transferring an incident laser, "$n_2$" representing a refractive index of a medium for transferring a diffraction laser, "$\theta_{inc}$" representing an incident angle of the incident laser, and "$\theta_{dif}$" representing a diffraction angle of the diffraction laser.

10. The electronic incense censer of claim 8, wherein the laser LED faces a center of the diffraction grating.

11. The electronic incense censer of claim 8, wherein the light calibrator is a lens for concentrating the split laser beams to cause the split laser beams to align with the hollow tubes, respectively.

12. The electronic incense censer of claim 11, wherein a center of the lens is aligned with the center of the diffraction grating.

13. The electronic incense of claim 6, wherein the top end of the hollow tube and the sheath coated on an outer sidewall of the hollow tube is totally covered by the light outputting portion.

* * * * *